United States Patent
Troosters et al.

(10) Patent No.: US 9,248,274 B2
(45) Date of Patent: Feb. 2, 2016

(54) NEUROSTIMULATOR AND METHOD FOR REGULATING SAME

(75) Inventors: Michel Troosters, Dion-Valmont (BE); Jean Delbeke, Kraainem (BE); Pascal Doguet, Tangissart (BE); Herve Mevel, Louvain-la-Neuve (BE)

(73) Assignee: SORIN CRM SAS, Clamart (FR)

( * ) Notice: Subject to any disclaimer, the term of this patent is extended or adjusted under 35 U.S.C. 154(b) by 271 days.

(21) Appl. No.: 12/681,869

(22) PCT Filed: Oct. 10, 2007

(86) PCT No.: PCT/EP2007/060792
§ 371 (c)(1),
(2), (4) Date: Apr. 6, 2010

(87) PCT Pub. No.: WO2009/046764
PCT Pub. Date: Apr. 16, 2009

(65) Prior Publication Data
US 2010/0222844 A1    Sep. 2, 2010

(51) Int. Cl.
*A61N 1/00* (2006.01)
*A61N 1/05* (2006.01)
*A61N 1/36* (2006.01)

(52) U.S. Cl.
CPC ............ *A61N 1/0529* (2013.01); *A61N 1/0556* (2013.01); *A61N 1/3605* (2013.01)

(58) Field of Classification Search
CPC . A61N 5/0622; A61N 1/365; A61N 1/36114; A61B 5/05
USPC ................................................. 607/40, 116
See application file for complete search history.

(56) References Cited

U.S. PATENT DOCUMENTS

| 4,602,624 A | 7/1986 | Naples et al. |
| 5,824,027 A | 10/1998 | Hoffer et al. |

(Continued)

FOREIGN PATENT DOCUMENTS

| EP | 0 753 284 | 3/1999 |
| WO | WO 01/28622 | 4/2001 |

(Continued)

OTHER PUBLICATIONS

Demichele et al., "Stimulus-Resistant Neural Recording Amplifier"; Engineering in Medicine and Biology Society, 2003. Proceedings of the 25th Annual International Conference of the IEEE vol. 4, Issue, Sep. 17-21, 2003 pp. 3329-3332 vol. 4, 4 pages.

(Continued)

*Primary Examiner* — Christopher D Koharski
*Assistant Examiner* — Michael D Abreu
(74) *Attorney, Agent, or Firm* — Foley & Lardner LLP

(57) ABSTRACT

The present invention relates to an electrode (30,30') for implantation in contact with a neural tissue, said electrode extending along an axis, said neural tissue being capable of generating one or more action potentials, and said one or more action potentials propagating with a given speed in said neural tissue. The electrode comprises a carrier (31, 31') of biocompatible electrically insulating material; stimulation electrode contacts (32a; 32'a; 32b; 32'b) deposited on a surface of said carrier (31, 31') for applying an electrical stimulation to said neural tissue so as to generate, after a given latency time, a compound action potential when stimulated by said electrical stimulation; one or more sensing electrode contacts (33a; 33b; 33c; 33'a; 33'b; 33'c) deposited on said surface of said carrier and provided at a distance from said stimulation electrode contacts, said sensing electrode contacts being adapted to be connected to measuring means (23) having a given inactive period. The invention includes means to reduce the stimulation artifact. The invention also relates to an apparatus (20) and method for using various signals obtained from the stimulation probe itself and used to control the parameters of the current pulses applied to the electrodes.

11 Claims, 7 Drawing Sheets

(56) References Cited

U.S. PATENT DOCUMENTS

| | | | |
|---|---|---|---|
| 5,857,980 A * | 1/1999 | Wilson | 600/546 |
| 5,913,882 A | 6/1999 | King | |
| 6,529,774 B1 | 3/2003 | Greene | |
| 7,167,751 B1 | 1/2007 | Whitehurst et al. | |
| 7,310,557 B2 * | 12/2007 | Maschino et al. | 607/40 |
| 7,561,918 B2 | 7/2009 | Armstrong | |
| 2002/0183817 A1 | 12/2002 | Van Venrooij et al. | |
| 2003/0040785 A1 * | 2/2003 | Maschino et al. | 607/118 |
| 2004/0010303 A1 | 1/2004 | Bolea et al. | |
| 2005/0137645 A1 | 6/2005 | Voipio et al. | |
| 2006/0030919 A1 | 2/2006 | Mrva et al. | |
| 2006/0167497 A1 | 7/2006 | Armstrong | |
| 2008/0046016 A1 * | 2/2008 | Ben-David et al. | 607/6 |

FOREIGN PATENT DOCUMENTS

| | | |
|---|---|---|
| WO | WO-01/60445 | 8/2001 |
| WO | WO 2004/034880 | 4/2004 |
| WO | WO-2004/087256 | 10/2004 |
| WO | WO-2006/017277 | 2/2006 |
| WO | WO 2006/041870 | 4/2006 |
| WO | WO 2007/064739 | 6/2007 |
| WO | WO-2009/046764 | 4/2009 |

OTHER PUBLICATIONS

Office Action on European Application No. 07821159.6-1657, dated Jan. 3, 2014, 7 pages.

* cited by examiner

NEUROSTIMULATOR AND METHOD FOR REGULATING SAME

This application is a 371 application of PCT/EP2007/060792, filed Oct. 10, 2007.

TECHNICAL FIELD

The present invention relates to the field of neurological implants. More particularly, it relates to the field of stimulators for neural tissue and nerves, including cranial and peripheral nerves. More specifically, the present invention relates to a neurostimulator and a method for integrated regulation of the intensity, regimen, shape, pulse duration, frequency, train rate and train length of electrical stimulations generated by this neurostimulator.

DESCRIPTION OF RELATED ART

Nowadays, the nerve stimulation is largely utilized in several applications for treating or monitoring a variety of medical, psychiatric, or neurological disorders. In particular, vagus nerve stimulation techniques as well as deep brain stimulation techniques have been considerably studied.

Vagus nerve (also referred as pneumogastric nerve or cranial nerve X) is the tenth of twelve paired cranial nerves. It is characterized in that it is the only nerve that starts in the brainstem, i.e. within the medulla oblongata, and extends, through the jugular foramen, down below the head, to the abdomen. In particular, it is responsible for controlling and/or receiving feedback from various glands, the heart, pharynx, larynx, aortic and carotid pressure sensors, lungs, stomach, ureters, and so on. Because of its broad number of functions with respect to a range of body systems, vagus nerve is preferred in many applications for purposes of modulating the functions of designated organs or portions of the central nervous system.

It is well known that neurons typically propagate signals along their axon. Peripheral nerve fibers that propagate signals away from the central nervous system (i.e., the brain and the spinal cord) and towards the periphery and viscera are referred to as efferent nerve fibers. Peripheral nerve fibers that propagate signals away from the periphery and viscera and towards the central nervous system are referred to as afferent nerve fibers.

Efferent impulses may produce a variety of actions, from movement of a muscle to initiation of changes in the heart rate or force of contraction or in the level of constriction of the vascular smooth muscle in arterioles. Through increasing or decreasing the activity of efferent fibers, the central nervous system can, for example, alter the blood pressure by changing the characteristics of the cardiovascular system.

Afferent impulses from specialized nerve endings or receptors inform the controlling neurons in the central nervous system about characteristics of the system, e.g., if a limb is feeling pain. Most peripheral nerves contain both afferent and efferent nerve fibers.

An individual neuron typically consists of a soma (i.e. cell body), which contains the nucleus of the cell; dendrites, which receive input from pre-synaptic neurons; and an axon, which send signals via axon terminals (i.e. the distal portion of the axon) to post-synaptic neurons (or to effector cells, such as muscle fibers). An action potential is initiated at the initial segment of the axon (i.e. the proximal portion of the axon) when triggered by input from the dendrites.

An action potential is an electrochemical signal that propagates from the initial segment down the axon to the axon terminals. Such propagation is referred to as orthodromic, which is defined as "of, relating to, or inducing nerve impulses along an axon in the normal direction". Action potential propagation in the opposite direction is referred to as antidromic, which is defined as "proceeding or conducting in a direction opposite to the usual one used especially of a nerve impulse or fiber".

When a neuron is at rest (i.e., there is no propagation of an action potential), the inside of the axon is negatively charged with respect to the outside of the neuron, i.e., the membrane of the axon is at a negative resting potential. Said negative resting potential is typically between −80 and −60 mV. Through chemical connections known as synapses, any given neuron receives from other neurons excitatory and inhibitory input signals or stimuli. A neuron integrates the excitatory and inhibitory input signals it receives, and generates or fires a series of action potentials when the integration exceeds a threshold potential of about −20 mV. A neural firing threshold may lead the inside of the axon to a charge of about +30 mV. Action potentials propagate to the neuron's synapses, where they are conveyed to other neurons to which the neuron is synaptically connected.

The deep-brain stimulation (DBS) was first developed in France in 1987 and developed from the so-called ablative, or lesioning, surgeries in which surgeons use heat probes to burn and permanently damage small regions of the brain. These same brain regions are now targeted with DBS, but instead of destroying tissue, implanted electrodes apply pulses of electricity. DBS electrodes typically have a diameter of about 1.30 millimeter and are connected to wires that snake from the skull, behind the ear and down to a small battery-run power pack which is typically installed in the chest. When the generator is switched on, it delivers continuous low-voltage electrical pulses to the brain.

PRIOR ART DISCUSSION

A neurostimulator is an electronic device capable of applying a neural stimulation signal to a nerve or brain tissue through one or more electrodes. A neural stimulation signal typically comprises a series or train of electrical or magnetic pulses that can induce action potentials in some neurons (or axons) within a target neural population. These pulses may be defined or described in accordance with stimulation signal parameters including pulse amplitude, pulse frequency, duty cycle, stimulation signal duration, and/or other parameters. Although electrical or magnetic stimulation of neural tissue is intended to produce a type of therapeutic, rehabilitative, or restorative neural activity, however most of such stimulations represents a waste of battery current and may result in collateral neural activity. In particular, neural stimulation delivered beyond a certain value of intensity, level, or amplitude can produce seizure activity and/or other types of collateral activity, which may be undesirable and/or inconvenient in a neural stimulation situation. It is evident that the control and the regulation of the intensity, level, or amplitude of such electrical stimulations represent a very important aspect.

The traditional method for obtaining a stimulation of sufficient magnitude (strength) consists in increasing progressively the current pulse intensity, or the pulse duration, or the frequency, or the pulse train length of the electrical stimulation and monitoring physiological parameters, disease state parameters and/or reactions of the patient. For example, the amplitude or strength of the stimulation will be reduced according to collateral sensations reported by the patient who has noticed, perceived or experienced a physical sensation due to that stimulation. Such a regulation, which is typically defined as neural stimulation threshold test procedure, is evidently very uncomfortable for the patient and does not guarantee optimal therapeutic stimulation intensity. Furthermore, this regulation may create disturbance and, even pain, before the desired intensity is obtained. Also, the finally selected stimulation is more a reflection of the patient's sensitivity than a function of the effective nerve stimulation and, as a consequence, a stronger stimulation than required might be selected and used for long periods of time.

Another important limitation of current neurostimulators is represented by the so-called stimulation artifact. In order to study in vitro and in vivo neural activity, neuroscience researches are increasingly using both electrical stimulation and neural recording. Typically, the neural signals that are recorded are less than 10 μV and in order to be usable they have to be treated by special equipment, such as low-noise broadband amplifiers. However, when an electrical stimulation is applied to a tissue, the electrical field generated in the tissues by the stimulation artifact introduced into this tissue may be three or four orders of magnitude larger than normal activity of a neural population or compound action potential. As a consequence, this stimulation artifact instantly saturates the recording equipment which remains for a certain time inactive until the system regains its electrical equilibrium. This inactive period may be several hundred milliseconds long and can cause failures of the recording equipment. For more details concerning neural-recording amplifier systems one can refer, for example, to the document "Stimulus-Resistant neural Recording Amplifier"; DeMichele, G. A., Troyk, P. R.; Engineering in Medicine and Biology Society, 2003. Proceedings of the 25th Annual International Conference of the IEEE Volume 4, Issue, 17-21 Sep. 2003 Page(s): 3329-3332 Vol. 4.

It is known from document EP0753284 a single nerve compound action potential measuring apparatus. This apparatus comprises in particular means for separating and extracting the nerve compound action potential generated by a single neuron from other neurons. However, this apparatus does not provide means for monitoring the compound action potential of the entire nerve. Moreover, it does not comprise means for electrically stimulating the nerve.

It is known from document U.S. Pat. No. 4,602,624 an implantable cuff which fits around a nerve trunk. The cuff mainly comprises a self-curling sheet of non-conductive material which is self-biased to curl into a spiral or roll. It also comprises two electrodes (40, 50) for applying electrical impulses that are disposed on said self-curling sheet such that one extends peripherally around each of the larger and smaller diameter regions of the passage therethrough. However, this implantable cuff does not comprise means for monitoring the neural activity during the stimulations.

It is also known from document U.S. Pat. No. 7,167,751 a method of using a small implantable stimulator(s) with at least two electrodes small enough to have the electrodes located adjacent to the vagus nerve. The small stimulator provides means for stimulating the vagus nerve when desired. However, the regulation of the intensity and/or duration of electrical stimulation required to produce the desired effect is based on the state of the patient which is additionally or alternatively sensed.

Document US20050137645 discloses a method for adjusting the vagus nerve stimulation (VNS) signal induced by a stimulus generator implanted in a patient. However, the regulation of the intensity of the stimulation is based on the response of respiratory or physiological acid-base parameters of the patient.

Document WO01/60445 relates to methods and apparatuses for the detection of neural or muscular activity, analysis of the signals and the subsequent stimulating of neural or muscular tissue based thereon. This document discloses a combined sensing and stimulation electrode device mainly addressed to the hemiplegic drop foot. The device mainly comprises:

at least one neurosense electrode means capable of sensing a nerve signal from a peripheral nerve and at least one stimulation electrode means capable of stimulating a peripheral motor nerve fibre;

means for receiving and processing the sensed neurosignals to identify a signal indicative of a specific action, especially a component of the gait performed by the patient and for producing a control signal in response thereto;

means for operating the at least one stimulation electrode means in response to the control signal to produce a stimulation of a peripheral motor nerve fibre.

Neurosense electrode means and stimulation electrode means may be combined together in order to have a single electrode which, in combination with switching means, may perform stimulation or sensing of the neural activity of a nerve. However, this device does not provide a single cuff electrode that may simultaneously stimulate and record the effect of stimulations on said nerve. Predetermined stimulations are applied to a neural tissue or a muscular tissue at a selected time based on the signals detected by neurosense electrodes and based on the analysis of said signals. This device is capable of monitoring the neural activity without stimulations and provides, according to the prior art, an indirect measurement of the stimulation based on a quantitative representation of the level or "state" of the disease to be treated. This device does not provide a direct and qualitative measurement of the effect of the stimulation applied to a nerve. Furthermore, this device does not provide means for overcoming the stimulation artifact.

It is known from document WO2006/017277 a neurological control system for modulating activity of a nervous system component in the treatment of diseases in order to control a therapy. This neurological control system comprises several sensing electrodes contacts for evaluating a disease state and processes this information in order to control a treatment by applying neuromodulation stimulation. Similarly to the above discussed documents of the prior art, this device also performs indirect measurements of the applied stimulation by evaluating the disease state or the global therapeutic efficiency. In fact said sensing electrodes contacts explore effects of the stimulation at a certain distance from where the stimulation occurs, there where symptoms of the disease can be recorded. No verification of the immediate physiological effect of the applied stimulation is performed.

The present invention aims at providing a neurostimulator that overcomes the above-discussed drawbacks of the prior art. In particular, it is an object of the present invention to provide a neurostimulator wherein the regulation of the magnitude or strength of the electrical stimulation is no longer based on testing subjective perceptions of the patient or indirect measurements. More particularly, it is an object of the present invention to provide a more efficient and more reliable neurostimulator, in contrast with prior art, wherein the regulation of the stimulation strength is operated continuously and automatically without disturbing the patient. Moreover, it is an object of the present invention to provide a neurostimulator which avoids the drawback of stimulation artifact.

SUMMARY OF THE INVENTION

In a first aspect, the invention relates to an electrode for implantation in contact with a neural tissue, said electrode extending along an axis, said neural tissue being capable of generating one or more action potentials, said one or more action potentials propagating with a given speed in said neural tissue. The electrode comprises a carrier of biocompatible electrically insulating material; stimulation electrode contacts deposited on a surface of said carrier for applying an electrical stimulation to said neural tissue so as to generate, after a given latency time, a compound action potential when stimulated by said electrical stimulation; one or more sensing electrode contacts deposited on said surface of said carrier and provided at a distance from said stimulation electrode contacts, said sensing electrode contacts being adapted to be connected to measuring means having a given inactive period. According to the invention, the sensing electrode contacts are located at a predetermined distance $\Delta e$ from the stimulation electrode contacts so that said compound action potential, generated by said stimulation electrode contacts reaches said sensing electrode contacts when said inactive period of said measuring means is already elapsed.

In a first embodiment of the invention, the electrode comprises a cuff capable of fitting closely around a selected portion of an elongated nerve, said stimulation electrode contacts and sensing electrode contacts being deposited on a surface of said cuff in contact with said portion of the nerve.

Preferably, the distance $\Delta e$ in this first embodiment is comprised between 2 mm and 20 mm.

In a second embodiment of the invention, the carrier comprises a lead capable of being inserted into a portion of a brain tissue, said stimulation electrode contacts and sensing electrode contacts being deposited on a surface of said lead in contact with said portion of the brain tissue.

Preferably, the distance $\Delta e$ in this second embodiment is comprised between 1 mm and 15 mm.

6. In the second embodiment, the stimulation electrode contacts and sensing electrode contacts may be arranged alternately along said lead.

The lead may comprise a single stimulation electrode contact and a single sensing electrode contacts.

The lead may also comprise a single stimulation electrode contact and a pair of sensing electrode contacts arranged on opposite sides of said stimulation electrode contact.

The lead may also comprise a plurality of sensing electrode contacts arranged on a circumference of said lead.

In both embodiments of the invention, the sensing electrode contacts may form a tripole. In a tripole, one electrode is surrounded by two other electrodes connected electrically together.

The sensing electrode contacts may comprise a single electrode contact, a voltage reference being provided by an electrode contact located in a position remote from the electrode. The remote electrode contact may be the casing of a neurostimulation apparatus.

In a second aspect, the invention relates to a nerve stimulation apparatus for inducing electrical stimulations to a neural tissue, the apparatus comprising a generator for generating electrical stimulations having specified amplitude and shape; electrical connectors for connecting the apparatus to the electrode of the invention. According to the invention, the apparatus comprises means for controlling the amplitude and shape of said electrical stimulations in such a way that the amplitude of the compound action potential measured by sensing electrode contacts reaches an expected value within desired time constraints. By "shape" of the electrical stimulation, one understands in the present context the shape of a single pulse, as well as the duration of a pulse, the repetition rate, the pulse train duration or duty cycle for discontinuous stimulation and the modification of these in time.

The regulation means of the nerve stimulation apparatus may comprises a microcontroller for controlling the amplitude and shape of the electrical stimulations; an amplifier for amplifying and conditioning analog signals recorded by sensing electrode contacts and an analog/digital signal converter for converting amplified analog signals into digital signals.

In one embodiment of the nerve stimulation apparatus, the microcontroller comprises a programmed algorithm for automatically computing said specified amplitude and shape.

In another embodiment of the nerve stimulation apparatus, the microcontroller comprises means for exchanging information with an external output device for displaying the compound action potential and an external input device, whereby an operator adapts said specified amplitude and shape depending on the displayed compound action potential. The means for exchanging information may use wireless data exchange through an antenna system, as is well known in the art.

The amplifier may advantageously be a variable-gain amplifier, wherein the gain is controlled by the microcontroller through an input gain control line. Thereby, the input gain may be reduced to zero during the stimulation phase, and set to an appropriate value during the measurement phase.

The amplifier may also be provided with a short circuit next to its input ports, the short circuit being controlled the microcontroller through the input short circuit control line with the same purpose The power supply voltage of the amplifier may advantageously be selected at a value which is higher than the maximum voltage of stimulation pulses produced by said generator. Thereby, the risk of a saturation of the amplifier by the stimulation pulses is reduced.

The nerve stimulation apparatus may further comprise a high-pass filter between the sensing electrode contacts and the amplifier and/or a low-pass filter between the amplifier and the ND converter.

In a last aspect, the invention relates to a method for regulating the intensity of electrical stimulations generated by a nerve stimulation apparatus characterized in that it comprises the steps of: implanting an electrode of the invention in such a way as to be in contact with a portion of a neural tissue; applying electrical stimulations on said portion by means of stimulation electrode contacts; measuring the compound action potential generated by said stimulation electrode contacts through sensing electrode contacts and adjusting the amplitude and shape of said electrical stimulations in order to obtain a desired compound action potential.

Preferably, the step of applying electrical stimulations on said portion comprises applying a long-duration (t1), low-amplitude (A1) anodic phase and a subsequent relatively short-duration (t2), high-amplitude (A2) cathodic phase in order to activate the neural tissue at the very end of the charge balanced stimulation.

The anodic phase may be applied with a progressive amplitude in order to further avoid early tissue activation.

One may adjust the cathodic to anodic phase ratio in order to minimize the stimulus artifact, the anodic charge recuperation phase duration being equal or slightly smaller than the cathodic stimulating phase duration.

The method may further comprise the step of reducing the amplitude and shape of said electrical stimulations when the measured characteristics of the compound action potential or other measurements from the probe indicate that a predetermined safety limit is reached.

More preferably, the method may further comprise the step of measuring at least one of the following parameters: of said electrical stimulation: local DC potential values; stimulation voltage values; tissue impedance values, in order to determine said safety limit for guaranteeing the safety of said portion of neural tissue.

More preferably, the method further comprises the step of measuring the voltage applied by said generator to said stimulation electrode contacts in order to determine said safety limit for preventing the corrosion of said stimulation electrode contacts.

DETAILED DESCRIPTION OF THE INVENTION

First Embodiment of the Invention

Figure 1:
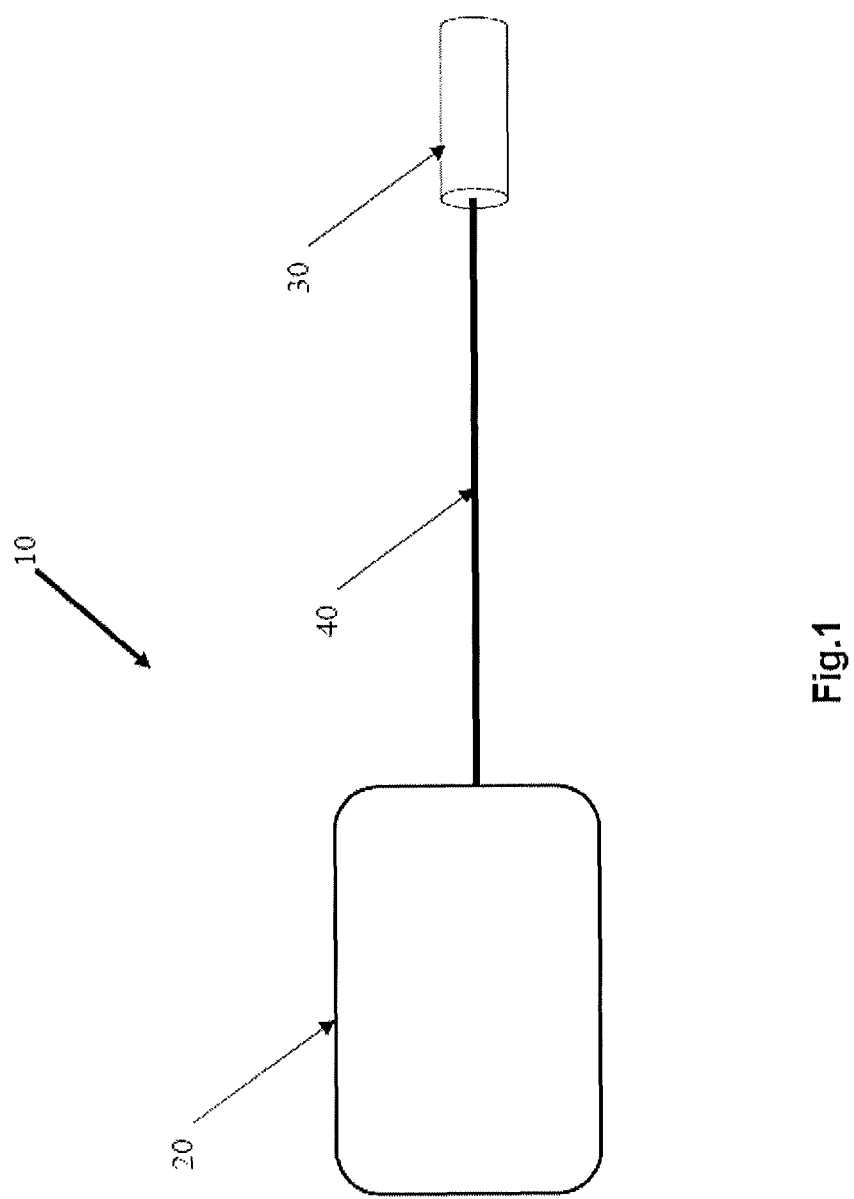
FIG. 1 illustrates a neurostimulator device according to a preferred embodiment of the present the invention.
Figure 2:
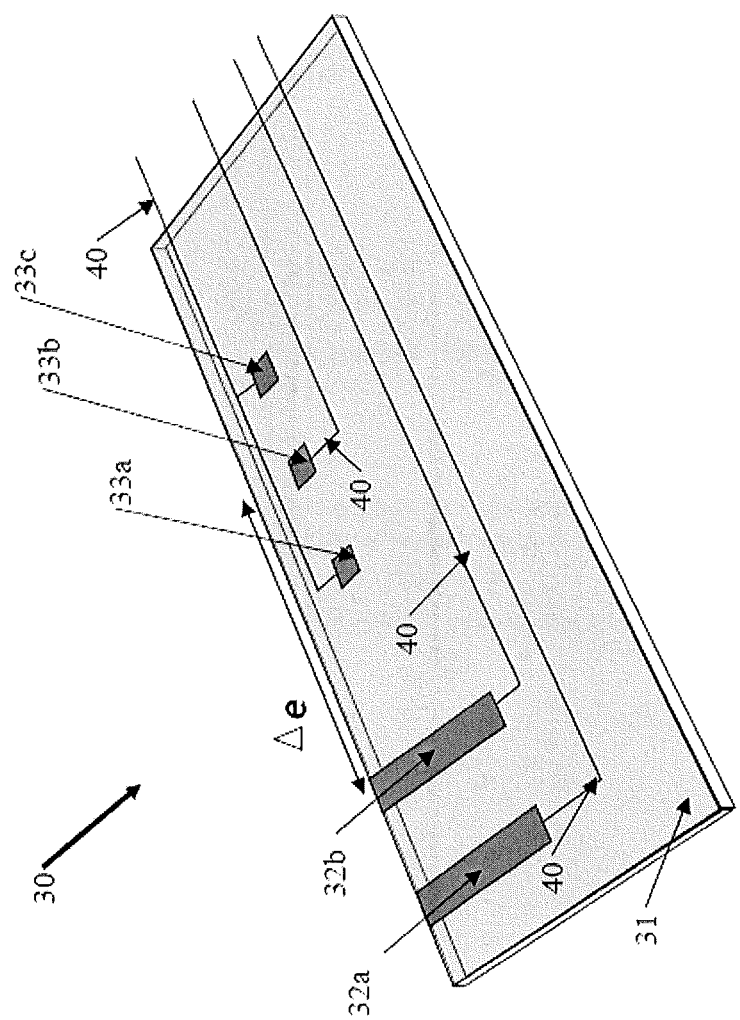
FIG. 2 and FIG. 3 show, respectively, a perspective view of a cuff electrode in an uncurled configuration and a perspective view of the same cuff electrode in a curled configuration, according to a first preferred embodiment of the present invention.
Figure 3:
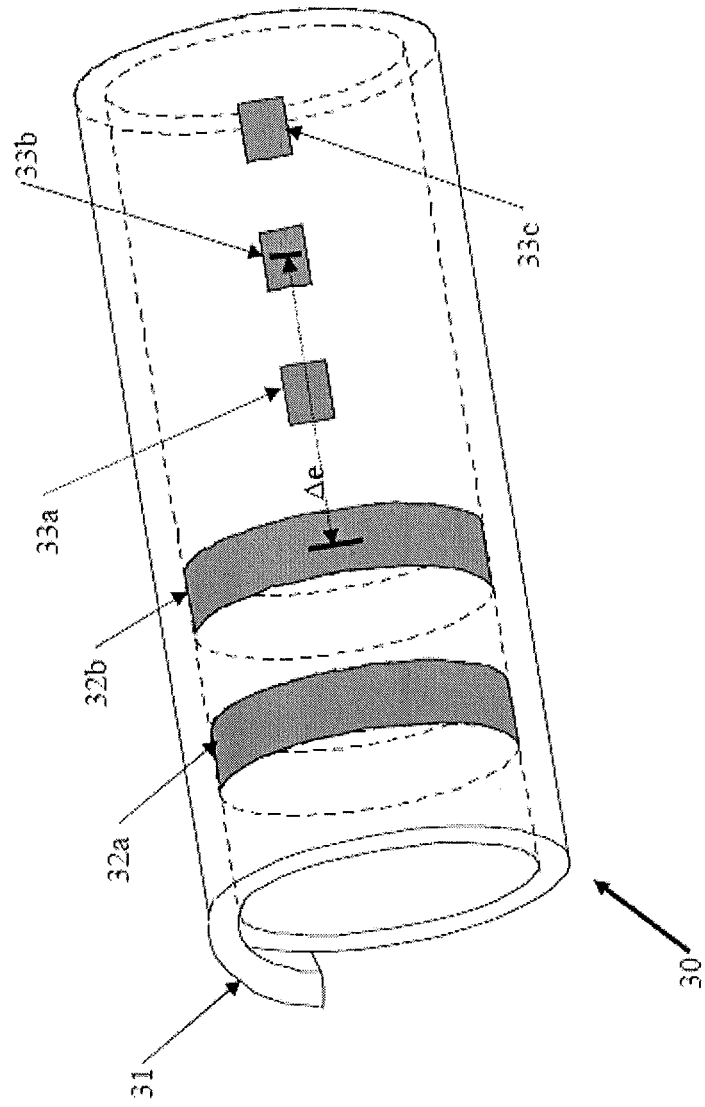

A neurostimulator for inducing electrical stimulations to a portion of a peripheral or cranial nerve, for example to a portion of the vagus nerve, according to a preferred embodiment of the present invention, is illustrated in FIG. 1. The neurostimulator 10 mainly comprises:
 a circuit enclosure 20;
 a cuff electrode 30 capable of fitting closely around a selected portion of said nerve;
 electrical connection wires 40 for connecting said cuff 30 to said circuit enclosure 20;

FIG. 2 and FIG. 3 show, respectively, a perspective view in a uncurled configuration and a perspective view in a curled configuration of the cuff electrode 30 of FIG. 1. Said cuff electrode 30 comprises:
 a carrier 31 of biocompatible electrically insulating material, such as silicone rubber for example;
 stimulation electrode contacts 32a, 32b deposited on said carrier 31, for applying an electrical stimulation to a selected portion of a nerve so as to generate a compound action potential;
 sensing electrode contacts 33a, 33b, 33c deposited on said carrier 31 provided along the direction of propagation of said compound action potential signals. Sensing electrode contacts 33a, 33b, 33c are positioned at a predetermined axial distance $\Delta e$ from the stimulation electrode contacts 32a, 32b or at specified positions with respect to the stimulation electrode contacts 32a, 32b or with respect to said selected portion of the nerve, as described in the following description.

Figure 4:
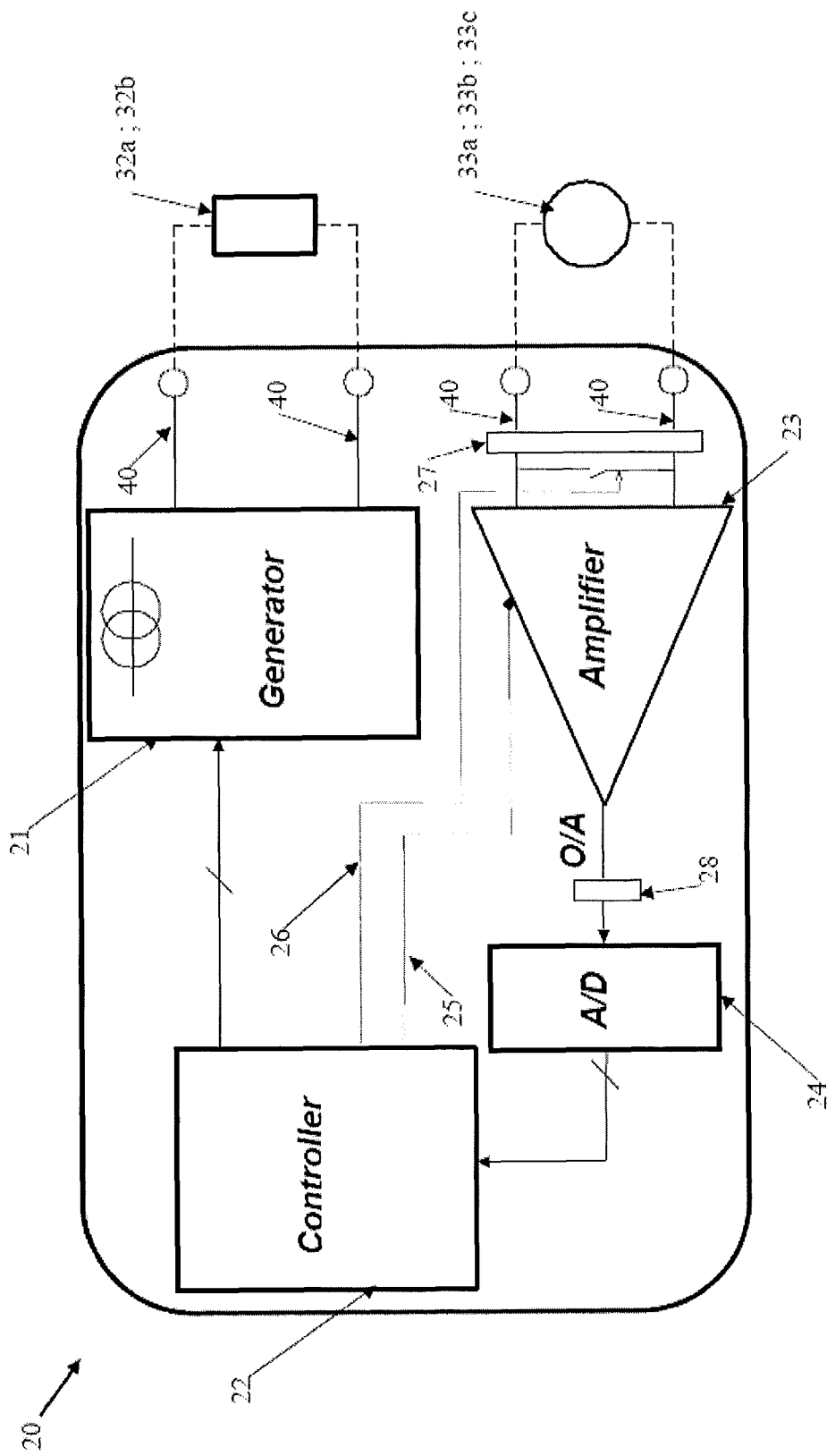
FIG. 4 shows a block diagram of the circuitry of the circuit enclosure of FIG. 1.

As shown in FIG. 4, the circuit enclosure 20 of FIG. 1 mainly comprises:
 a generator 21 of electrical stimulations capable of varying certain parameters of said electrical stimulations, such as, for example, intensity, shape, pulse duration, frequency, train rate, duty cycle and train length, etc;
 a micro controller 22 for automatically adjusting the parameters of said electrical stimulations, such as, for example, intensity, shape, pulse duration, frequency, train rate, duty cycle and train length, etc;
 an amplifier 23 for amplifying and conditioning analog signals recorded by sensing electrode contacts 33;
 an analog/digital signal converter 24 for converting amplified analogic signals into digital signals;

Analogic signals are recorded by sensing electrode contacts 33a, 33b, 33c, then amplified by amplifier 23 and finally converted into digital signals. The latter are the input for micro controller 22 which is capable of varying certain parameters of the electrical stimulations in such a way that the amplitude of the resulting compound action potential (or any other parameter including the local DC shift or the stimulus potential field, as measured by sensing electrode contacts 33, and the stimulation electrode potential) reaches an expected value within desired time constraints.

Sensing electrode contacts 33a, 33b, 33c are located at a predetermined axial distance $\Delta e$ from the stimulation electrode contacts 32a, 32b, as shown in FIG. 2. Sensing electrode contacts 33a, 33b, 33c form a tripole electrode contact with two dependant contacts 33a, 33c and an independent contact 33b located between said two dependent contacts 33a, 33c, as shown in FIG. 2 or FIG. 3. In particular, the distance $\Delta e$ between the central part of stimulation electrode contact 32b and the central part of sensing electrode contact 33b has been computed in such a way that compound action potential signals (generated by the stimulation electrode contacts 32a, 32b) reach the sensing electrode contacts 33b when the artifact period of the amplifier 23 is already elapsed, in order to insure correct measurements of the amplitude of the compound action potential. Typically, the artifact period lasts about 0.5 ms, the compound action potential speed is roughly 50 m/s and the latency time for a cell to generate said compound action potential is about 1 ms. According to a preferred embodiment of the invention, the predetermined distance $\Delta e$ is 10 mm, so that the compound action potential reaches the sensing electrode 33b after 1.2 ms, that is when the artifact period is already elapsed (0.7 ms later). As the compound action potential speed as well as the latency time of a cell may be different from nerve to nerve, the value of the distance $\Delta e$ may be different. It is however clear that different values of distance $\Delta e$ may be chosen without departing from the condition that action potential signals (generated by the stimulation electrode contacts 32a, 32b) reach the sensing electrode contacts 33b when the artifact period of the amplifier 23 is already elapsed.

An important aspect of the present invention should be highlighted. Contrary to prior art disclosures, sensing electrodes contacts, according to the invention, perform direct measurements of the stimulation effect, and such measurements are done in close proximity to the stimulation whose direct effect can be monitored. More particularly, direct effects of the stimulation over electrode potentials, generated field potential and neural tissue excitation are used to control the electrical stimulus. Therefore, accordingly, such a monitoring is not performed by evaluating the disease state; by contrast, the sensing electrodes contacts control directly the technical efficiency of the stimulation rather than the global therapeutic efficiency of the stimulation.

Figure 4A:
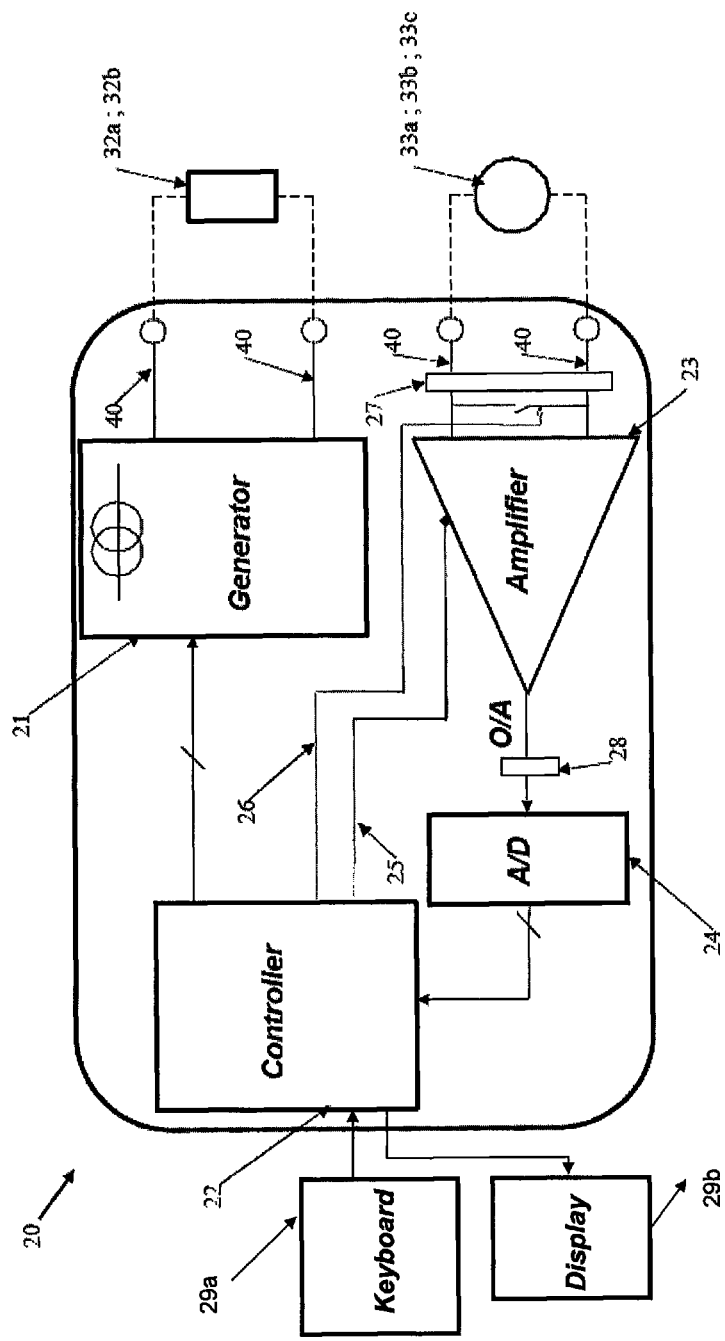
FIG. 4a shows a block diagram of the circuitry according to a variant of the circuit enclosure of FIG. 1.

In one embodiment of the apparatus, the controller comprises an algorithm adapted for automatically determining the amplitude and shape of the stimulation pulses. In this embodiment the apparatus may be used permanently by a patient. In another embodiment of the apparatus, as shown in FIG. 4a, a display device 29b displays the shape of the compound action potential measured by the sensing electrodes. An operator, or the patient himself, may then provide adapted instructions to the controller through an input device 29a. The input device 29a may be a small keyboard or a control panel with buttons and controls. When the apparatus 20 is implanted into the body of a patient, the communication between the apparatus 20, and the keyboard 29a and display 29b may occur through a wireless connection, using antennas.

In a variant of this preferred embodiment of the present invention, the neurostimulator 10 comprises a high-pass filter (27) between said amplifier (23) and said sensing electrode contacts (33a; 33b; 33c; 33'a; 33'b; 33'c) and/or a low-pass filter (28) between said amplifier (23) and said ND converter (24). In this case the amplifier 23 amplifies signals in a preferred frequency range.

Figure 5:
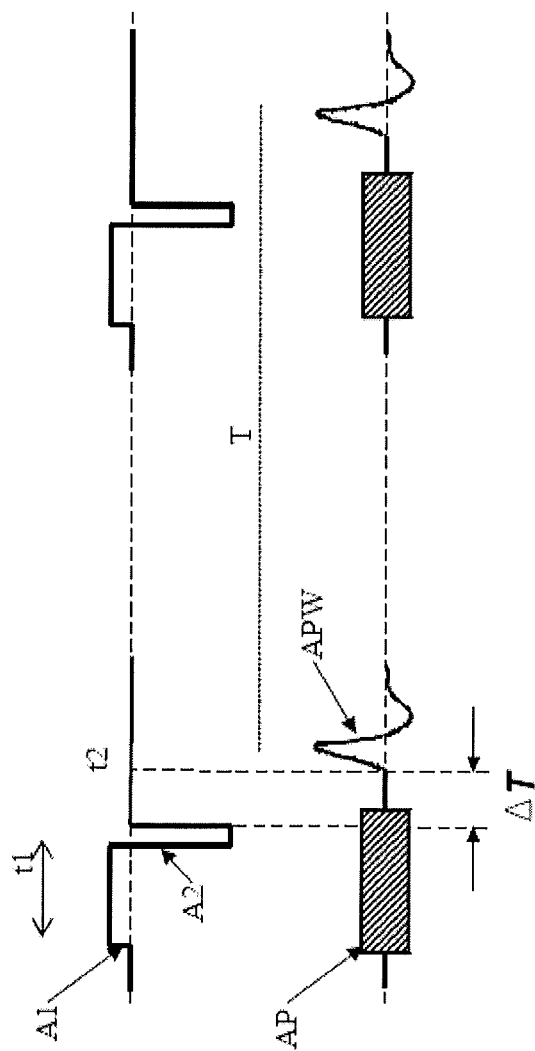
FIG. 5 is a schematic diagram of stimulation current waveforms and amplified compound action potential waveforms for the neurostimulator of FIG. 1.

FIG. 5 is a schematic diagram of stimulation current waveforms and amplified compound action potential waveforms for the neurostimulator 10 according to a preferred embodiment. The upper part of FIG. 5 shows two cycles of stimulation current waveforms which repeat with a period T and the corresponding lower part shows the artifact period AP and the compound action potential waveforms APW. Each cycle of stimulation (upper part) is characterized by a long-duration (t1), low-amplitude (A1) anodic phase and a subsequent relatively short-duration (t2), high-amplitude (A2) cathodic phase. The charge delivered by the anodic phase is equal in magnitude but opposite in polarity with respect to the charge delivered by the cathodic phase. In such a way it is possible to apply a charge-balanced stimulation which does not lead to tissue damage or electrodes corrosion. An important feature, according to this preferred embodiment of the present invention, is represented by the fact that the anodic phase is applied before the cathodic one, in contrast with prior art. In such a way with this particular choice, when the latency time required by the cells of the nerve for generating the compound action potential is elapsed and consequently the action potential is generated, the charge equilibrium between the two phases has been already re-established. Individual phases of the stimulation pulse are however not necessarily rectangular. For example, a progressive triangular anodic phase can be applied to further minimize the risk of neural activation during that phase. Also, various shapes of the cathodic phase can be used to optimize the selective activation of a subpopulation of axons or neurons.

According to a variant of this preferred embodiment, the amplifier 23 is a variable-gain amplifier, as shown in FIG. 4. The controller 22 is capable of varying the input gain of accelerator 23 through the input gain control line 25 during the stimulation artifact period. In such a way, during the stimulation artifact the amplifier 23 cannot be saturated.

According to a second variant of this preferred embodiment, in order not to saturate the amplifier 23, the power supply voltage of this amplifier 23 is selected at a value which is superior to the maximum voltage of stimulation pulses produced by generator 21.

According to another variant of this embodiment, in order not to saturate the amplifier 23, as shown in FIG. 4, the controller 22 is capable of controlling, through the input short circuit control line 26, a short circuit located between said amplifier 23 and sensing electrode contacts 33a, 33b, 33c. The controller 22 is capable of closing this short circuit during the artifact period, in order not to saturate the amplifier 23 and opening this short circuit at the end of the artifact period. With this arrangement, the invention permits to overcome the stimulation artifact drawback.

Second Embodiment of the Invention

According to a second preferred embodiment, the neurostimulator comprises, instead of the cuff electrode previously described, a deep brain stimulation electrode capable of being inserted stereotactically in close contact to a selected region of the brain.

Figure 6:
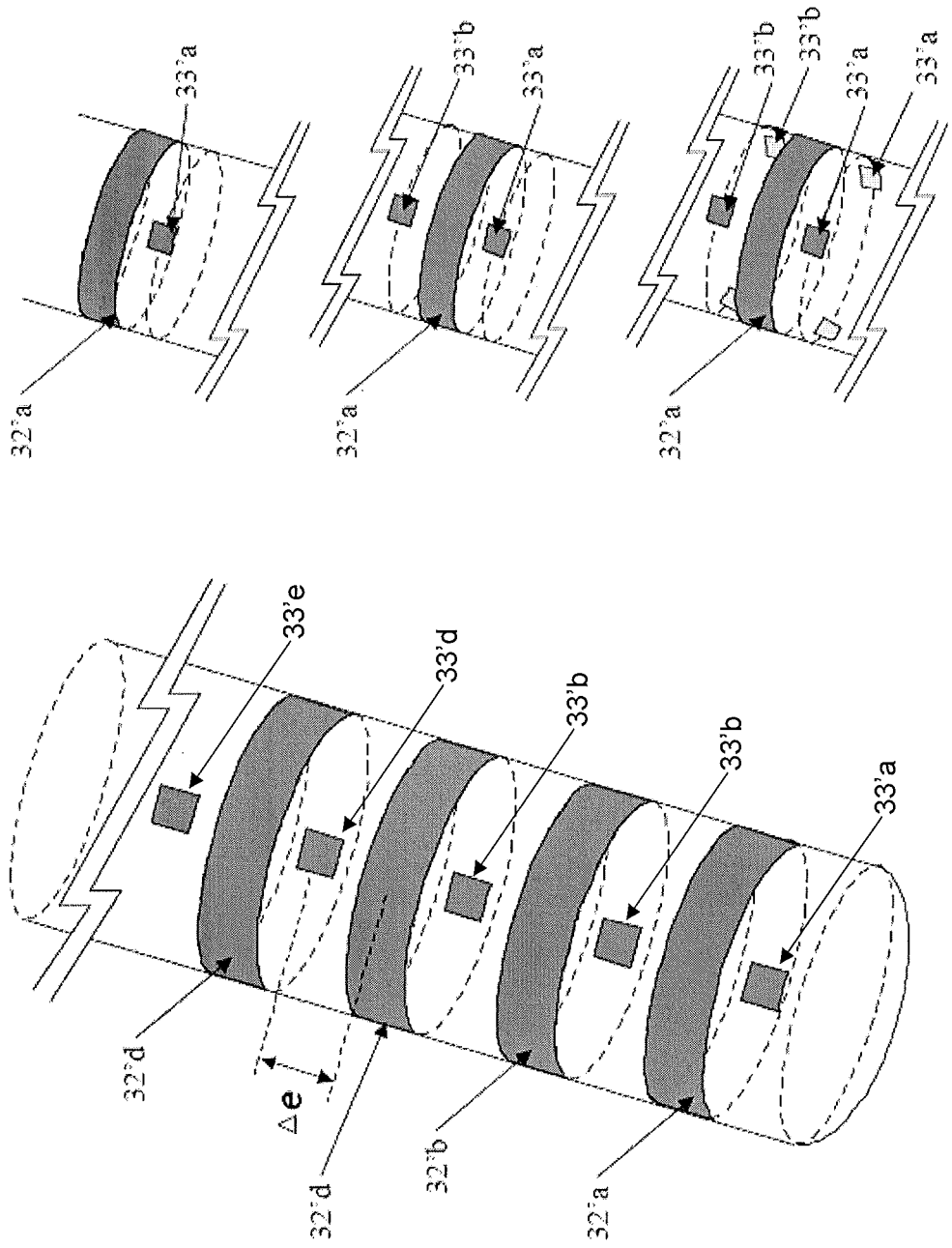
FIG. 6 shows a perspective view of a deep brain stimulation electrode according to a second preferred embodiment of the invention and different electrode contacts arrangements.

FIG. 6 shows a perspective view of such a deep brain stimulation electrode comprising a needle 30' and, similarly to the first preferred embodiment:
- a carrier 31' of biocompatible electrically insulating material, such as silicone rubber for example;
- ring-shaped stimulation electrode contacts 32'a, 32'b, 32'c, 32'd deposited on said carrier 31', for applying an electrical stimulation to said selected portion of the brain so as to generate a compound action potential which propagates in a tri-dimensional way;
- a plurality of small sensing electrode contacts 33'a, 33'b, 33'c, 33'd, 33'e deposited on said carrier 31' and positioned at a predetermined distance Δe from the stimulation electrode contacts 32'a, 32'b, 32'c, 32'd, similarly to the previous preferred embodiment.

According to different variants of this second preferred embodiment, the deep brain stimulation electrode may comprises a single ring-shaped stimulation electrode contact 32'a coupled to a single sensing electrode contact 33'a; or a single ring-shaped stimulation electrode contact 32'a coupled to two sensing electrode contacts 33'a, 33'b located up and down with respect to said stimulation electrode contact 32'a; or a single ring-shaped stimulation electrode contact 32'a coupled to three sensing electrode contacts 33'b located on said carrier 31' on one side of and at intervals of 120 degrees with respect to said stimulation electrode contact 32'a and with three other sensing electrode contacts 33'a located on said carrier 31' on the other side of and also at intervals of 120 degrees with respect to said stimulation electrode contact 32'a.

According to this second preferred embodiment, the neurostimulator may be used for example for the treatment of: Parkinson's disease, dyskinesia, essential tremor, epilepsy, pain, obsessive compulsive disorder (OCT), dystonia, torticollis, hemiparesis, speech impairment, cluster headaches, orthostatic hypotension, hypertension, tourette's syndrome, persistent vegetative state, and depression.

Depending on the particular disease, the deep brain stimulation electrode can be implanted (uni- or bilaterally) for example in subthalamic nucleus, globus pallidus, periventricular/periaqueducal gray matter (midbrain), thalamus, ventral intermediate nucleus of the thalamus, anterior thalamus, sensory thalamus (ventro-postero-lateral nucleus, centromedian thalamus, centromedian-parafascicular complex of thalamus, internal capsule, hypothalamus, mesencephalic reticular formation, cerebellum, caudate nucleus, hippocampus, amygdalo-hyppocampal region, neocortex, mamillary body, subgenual cingulated region (frontal cortex), nucleus accumbens.

Sensing electrode contacts, according to the invention, can be arranged in a number of montages in order to precisely localize the source of the signal being recorded. This includes monopolar montages whereby each derivation channel receives the signal from a single sensing contact of the electrode and is referred to a large distant contact higher up on the electrode shaft or on the stimulation enclosure. Alternatively, a large number of bipolar montages can be setup whereby each sensing contact is referred to another contact, each contact being connected to the active lead of one derivation and the reference lead of another one.

One advantage of the present invention is that it is capable of recording the synchronized compound action potentials generated by the stimulation for measuring the amplitude, shape and latency of the response.

Another advantage of the present invention is that it may be utilized for potentiometric sensing, e.g. chemical sensing, or for recording neural spontaneous electrical activity in order to evaluate the state of the system to be stimulated and so doing, avoid for example a level of damaging or unsafe stimulation.

The present invention may also be advantageously utilized for detecting or recording interference activity from physiological sources such as the ECG, plethysmographic activities, muscle potentials, etc or from external electrical sources including electrical transmission and fault detection.

The present invention may finally advantageously utilized for providing impedance measurements as well as for the determination of contact impedances and tissue impedance for evaluating the state of the electrode and/or of the tissue surrounding the electrode.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated. As a consequence, all modifications and alterations will occur to others upon reading and understanding the previous description of the invention. In particular, dimensions, materials, and other parameters, given in the above description may vary depending on the needs of the application.

The invention claimed is:

1. A nerve stimulation apparatus for inducing electrical stimulations to a neural tissue, the apparatus comprising:
   an electrode for implantation in contact with the neural tissue, said electrode comprising:
      a carrier of biocompatible electrically insulating material;
      two stimulation electrode contacts deposited on a surface of said carrier for applying an electrical stimulation to said neural tissue so as to generate, after a given latency time, a compound action potential when stimulated by said electrical stimulation;
      a plurality of sensing electrode contacts deposited on said surface of said carrier and provided at a distance from said stimulation electrode contacts, said sensing electrode contacts being adapted to be connected to a measuring means capable of being saturated by said electrical stimulation during an artifact period;
   wherein said sensing electrode contacts form a tripole comprising one central independent sensing electrode contact located between two other dependent sensing electrode contacts;
   wherein said sensing electrode contacts are located at a predetermined distance $\Delta e$ between 2 mm and 20 mm from the stimulation electrode contacts so that said compound action potential generated by said stimulation electrode contacts reaches said sensing electrode contacts when said artifact period of said measuring means is already elapsed; and
   wherein the predetermined distance $\Delta e$ is measured between a central part of the central independent sensing electrode and a central part of the stimulation electrode contact that is closest to the central independent sensing electrode contact.

2. The nerve stimulation apparatus of claim 1,
   wherein the carrier is configured to form a cuff capable of fitting closely around a selected portion of an elongated nerve, said stimulation electrode contacts and sensing electrode contacts positioned to be placed in contact with said portion of the nerve when implanted; and
   wherein said nerve stimulation apparatus further comprises:
   an amplifier for amplifying and conditioning analog signals recorded by sensing electrode contacts;
   an analog/digital signal converter for converting amplified analog signals into digital signals; and
   a microcontroller for receiving the digital signals and controlling the amplitude and shape of said electrical stimulations in such a way that the amplitude of the compound action potential measured by sensing electrode contacts reaches an expected value within desired time constraints.

3. The nerve stimulation apparatus of claim 2, wherein said microcontroller comprises a programmed algorithm for automatically computing said specified amplitude and shape.

4. The nerve stimulation apparatus of claim 2, wherein said microcontroller comprises means for exchanging information with an external output device for displaying the compound action potential and an external input device, whereby an operator adapts said specified amplitude and shape depending on the displayed compound action potential.

5. The nerve stimulation apparatus of claim 2, wherein said amplifier is a variable-gain amplifier, wherein said gain is controlled by said microcontroller through input gain control line.

6. The nerve stimulation apparatus of claim 2 wherein said amplifier is provided with a short circuit next to its input ports, said short circuit being controlled by said microcontroller through the input short circuit control line.

7. The nerve stimulation apparatus of claim 2 wherein the power supply voltage of said amplifier is selected at a value which is higher than the maximum voltage of stimulation pulses produced by said generator.

8. The nerve stimulation apparatus of claim 2 further comprising a high-pass filter between said amplifier and said sensing electrode contacts and/or a low-pass filter between said amplifier and said analog/digital signal converter.

9. The nerve stimulation apparatus of claim 1, wherein the carrier is configured to form a cuff capable of fitting closely around a selected portion of an elongated nerve, and wherein said stimulation electrode contacts form a closed loop on an inner surface of said cuff.

10. The nerve stimulation apparatus of claim 1, wherein said distance $\Delta e$ is equal to 10 mm.

11. The nerve stimulation apparatus of claim 1, further comprising:
   a generator for generating electrical stimulations having specified amplitude and shape;
   an electrical connector for connecting the generator to the electrode; and
   means for controlling the amplitude and shape of said electrical stimulations in such a way that the amplitude of the compound action potential measured by sensing electrode contacts reaches an expected value within desired time constraints.

* * * * *